US00PP12362P2

(12) United States Plant Patent
Utecht

(10) Patent No.: US PP12,362 P2
(45) Date of Patent: Jan. 22, 2002

(54) GERANIUM PLANT NAMED 'FISROROSE'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/632,244

(22) Filed: Aug. 3, 2000

(51) Int. Cl.[7] ..... A01H 5/00
(52) U.S. Cl. ..... Plt./328
(58) Field of Search ..... Plt./327, 328

(56) References Cited

PUBLICATIONS

GTITM UPOVROM Citation For 'FISROROSE' as per QZ PBR 980825; Jun. 15, 1998.*
2001 Fischer–Schmüllung Plant Alliance Catalog featuring 'Rocky Mountain Jazz' ('FISROROSE') on p. 7.*
Swiss Application for 'FISROROSE' (Apr. 22, 1999).*
European Union Application for 'FISHROROSE' (Aug. 17, 1998).*
European Union Grant for 'FISROROSE' (Aug. 16, 1999).*
German Application for 'FISROROSE' (Aug. 15, 1997).*
German Denomination for 'FISROROSE' (Jul. 15, 1998).*
German Grant for 'FISROROSE' (Jan. 15, 1999).*
Canadian Application, Denomination, Plant Varieties Journal No. 33, Oct. 1999 Canada.*

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fisrorose', as described and illustrated, and particularly characterized by the combined features of intense, salmon-pink, flower color, large, cup-shaped flowers, luxuriant, medium-green foliage with strong zonation, medium to tall plant habit, and early spring flowering response.

1 Drawing Sheet

BACKGROUND OF THE INVENTION

The present invention relates to a new and distinct cultivar of geranium plant, botanically known as *Pelargonium zonale*, and hereinafter referred to by the cultivar name 'Fisrorose'.

'Fisrorose' is a product of a planned breeding program which had the objective of creating new geranium varieties with salmon-pink to deep salmon, semi-double flowers, zoned foliage, and medium-tall plant habit.

'Fisrorose' originated from a hybridization made by the inventor, Angelika Utecht, in a controlled breeding program in Galdar, Gran Canaria, Spain, in 1992. The female parent was a hybrid seedling, designated no. 1061-1 (unpatented), characterized by large, red, semi-double flowers, large, relatively light-green foliage with strong zonation, and vigorous growth. The male parent was the commercial variety 'Penve' (U.S. Plant Pat. No. 9,970), characterized by purple-pink, semi-double flowers, medium-green foliage with slight zonation, and early flowering response.

'Fisrorose' was selected as one flowering plant within the progency of the stated cross by the inventor, Angelika Utecht, in 1993 in a controlled environment in Galdar, Gran Canaria, Spain.

The first act of asexual reproduction of 'Fisrorose' was accomplished when vegetative cuttings were taken from the initial selection in autumn 1993 in a controlled environment in Galdar, Gran Canaria, Spain, by, or under the supervision of, Angelika Utecht. Horticultural examination of plants grown from cuttings of the plant, initiated in May 1995 in Hillscheid, Germany, and continuing thereafter, has demonstrated that the combination of characteristics as herein disclosed for 'Fisrorose' are firmly fixed and are retained through successive generations of asexual reproduction.

BRIEF DESCRIPTION OF THE INVENTION

The following traits have been repeatedly observed and are determined to be basic characteristics of 'Fisrorose', which in combination distinguish this geranium as a new and distinct cultivar:

1. Intense salmon-pink to bluish-pink flower color;
2. Large, cup-shaped, semi-double flowers in wide umbels;
3. Relatively large, medium-green foliage with strong zonation;
4. Moderately vigorous growth; and
5. Early spring flowering response.

'Fisrorose' has not been observed under all possible environmental conditions. The phenotype of the new cultivar may vary significantly with variations in environment such as temperature, light intensity and day length without any change in the genotype. The following observations, measurements, and comparisions describe plants grown in Hillscheid, Germany, and in Langley, British Columbia, Canada, under greenhouse conditions which approximate those generally used in commercial practice.

Of the many commercial cultivars known to the inventor, the most meaningful comparison to be made with 'Fisrorose', are to the cultivars 'Fisplosive' (U.S. Plant Pat. No. 9,388) and 'Americana Salmon' (U.S. Plant Pat. No. 7,933). 'Fisrorose' could, however, be compared with the cultivars 'Fisplosive' (U.S. Plant Pat. No. 9,388) or 'Americana Salmon' (U.S. Plant Pat. No. 7,933). In comparison to 'Fisplosive', 'Fisrorose' has a slightly less bluish, more salmon tone of flower color, medium-green foliage with stronger zonation, and a more vigorous growth habit. In comparison to 'Americana Salmon', 'Fisrorose' has a slightly more intense, pinker flower color, larger flowers, shorter peduncles, and stronger zonation of foliage.

BRIEF DESCRIPTION OF THE DRAWING

The accompanying photographic illustration shows typical flower and foliage characteristics of 'Fisrorose' with colors being as true as possible with an illustration of this type.

DETAILED BOTANICAL DESCRIPTION

The measurements were taken in Langley, British Columbia, Canada, on Jun. 15, 1999, 12 weeks after planting of rooted cuttings into 15-cm pots. The plants had not been pinched. In the following description, color references are made to The Royal Horticultural Society (R.H.S.) Colour Chart. The color values were determined indoors from plants developed in a greenhouse in May 1999 in Hillscheid, Germany.

CLASSIFICATION

Botanical: A hybrid of the species *Pelargonium zonal L'Hérit* .

Commercial: Zonal geranium. cv. 'Fisrorose'.

INFLORESCENCE

Umbel:

*Shape.*—Almost semi-spherical.

*Average diameter.*—101 mm.

*Average depth.*—58 mm.

*Peduncle length.*—175 mm.

*Peduncle color.*—Light-green, color varies between RHS 143 A and RHS 144 A, slight infusion of anthocyanin may occur RHS 179 B.

*Pedicel length.*—29 mm.

*Pedicel color.*—Base is green RHS 143 C, middle part is brownish-red, RHS 181 A, and upper part is RHS 184 A.

*Number of flowers per umbel.*—Approximately 30–35.

*Lastingness of umbel.*—Approximately 18–20 days at 18° C.

Corolla:

*Average diameter.*—52 mm.

*Form.*—Semi-double.

*Shape.*—Large, nearly round, cup-shaped.

*Number of petals.*—7–9.

*Size of petals.*—Upper petals 28–30 mm long, 23–25 mm wide; lower petals 25–27 mm long, 25 mm wide.

*Shape of petals.*—Obovate, upper end rounded, attenuate bae, margin entire but slightly dentated.

*Number of petaloids.*—0–2.

*Color of petaloids.*—Upper surface RHS 52 B, lower surface RHS 52 C, base is pale pink, RHS 56 A.

*Color (general tonality from a distance of three meters)* .—Intense salmon with a slightly variable bluish-pink hue.

*Color of upper petals.*—RHS 52 C.

*Markings of upper petals.*—Slightly lighter colored area RHS 55 B at the base with weak, pink veins RHS 54 A.

*Color of lower petals.*—RHS 52 C.

*Color of lower surface of petals.*—Mainly RHS 52 C, partly more intense.

*Color of sepals.*—Outer surface mainly reddish RHS 181 B with green tips RHS 143 B; inner surface reddish RHS 179 A with green tips RHS 143 C.

*Size of sepals.*—11–12 mm long, 4–5 mm wide for the largest upper sepal, 2–3 mm wide for other sepals.

*Shape of sepals.*—Linear to lanceolate, truncate base, acute tip, surface weak with pubescence, margin entire.

*Number of sepals.*—5.

Bud (just before petals unfold):

*Shape.*—Elliptical.

*Color (sepals).*—Green, RHS 143 A, with infusion of anthocyanin RHS 179 A at the base.

*Color (petals).*—Salmon-pink, about RHS 52 C.

*Length.*—15 mm.

*Width.*—8–9 mm.

Reproductive organs:

*Androecium.*—Normally, 7 fertile anthers, white to light-pink filament, yellow-orange pollen RHS 33 A, plentiful in amount.

*Gynoecium.*—5–6 lobed stigma, red stigma and filament, one pistil per flower.

*Fertility/seed set.*—A few seeds may occasionally be developed; oblong in shape, 4–5 mm in length, brown RHS 177 B.

Spring flowering response period: In Hillscheid, Germany, in 1999, plants had on average 1.0 flowers opened 8 weeks after planting or rooted cuttings.

Outdoor flower production: Fair, the flower count in 1999, in Hillscheid, Germany, indicated on average about 3 inflorescences per plant in mid-May.

Durability: Good shatter resistance and relatively good rain resistance due to the open cup-shape of the flower; flower color somewhat variable.

Lastingness of individual bloom: Approximately 9 days at 18° C.

Fragrance: None.

PLANT

Foliage:

*Form.*—Kidney-shaped, with open base.

*Margin.*—Bicrenated.

*Size of leaf.*—Relatively large, 100–110 mm wide, 65 mm long.

*Color of upper surface.*—Medium-green, approximately from RHS 137 B to RHS 137 C.

*Color of lower surface.*—Lighter green, near RHS 137 D.

*Zonation.*—Strong, but not very wide ring, dark-brown colored, about RHS 200 B.

*Petiole size.*—60–70 mm in length, 3 mm in diameter.

*Petiole color.*—RHS 143 C.

General appearance and form:

*Internode length.*—10–20 mm.

*Branching pattern.*—7.1 branches.

*Plant size.*—21.0 cm high from the soil surface to the surface of the foliage canopy (without the inflorescence) and 37.3 cm wide.

Disease/pest resistance/susceptibility: None observed to date.

I claim:

1. A new and distinct cultivar of geranium plant named 'Fisrorose', as described and illustrated.

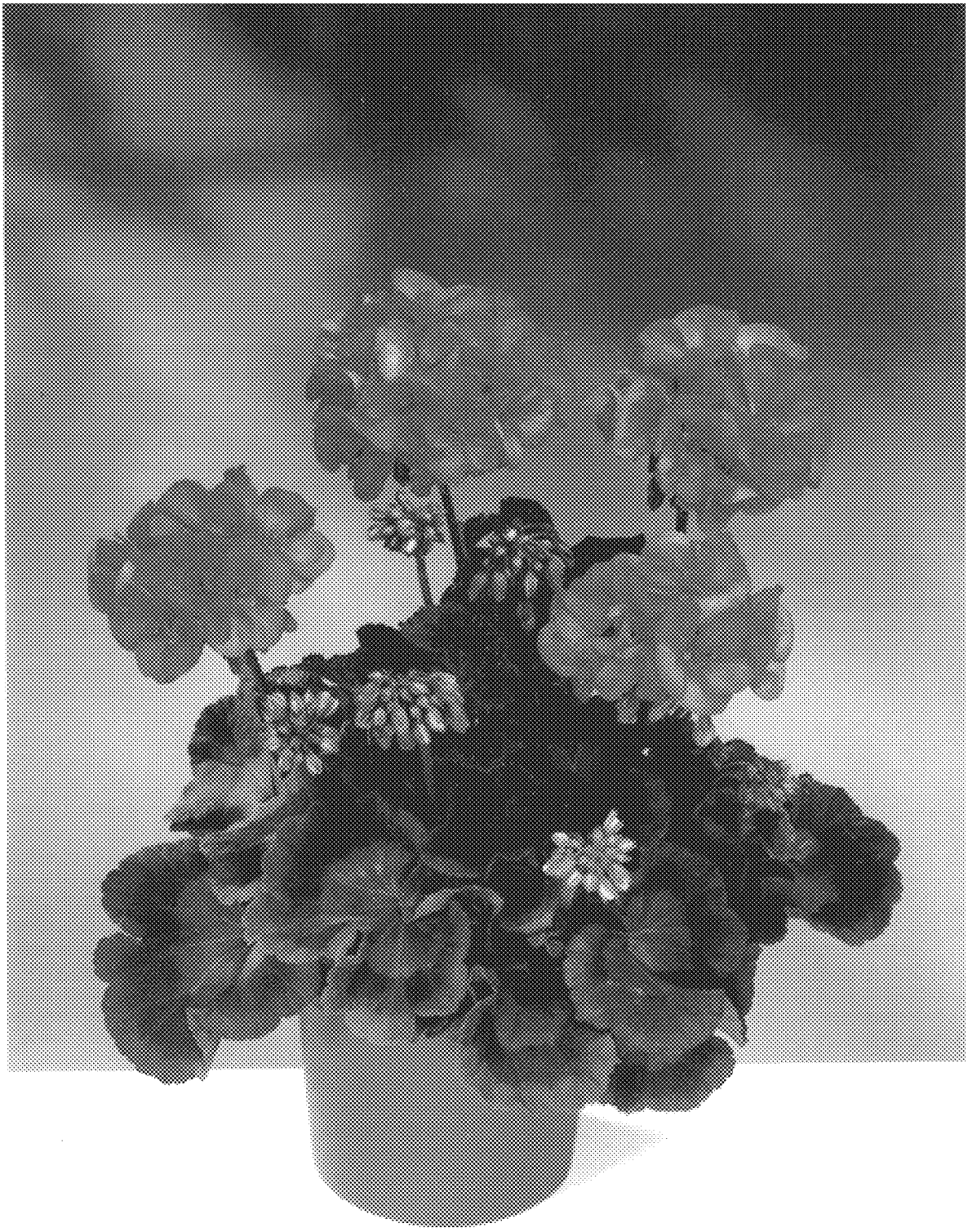

* * * * *